United States Patent [19]

Mrozik

[11] 3,953,492

[45] Apr. 27, 1976

[54] ANTHELMINTIC SUBSTITUTED SULFONAMIDE DERIVATIVES

[75] Inventor: Helmut H. Mrozik, Matawan, N.J.

[73] Assignee: Merck & Co., Inc., Rahway, N.J.

[22] Filed: Mar. 27, 1975

[21] Appl. No.: 562,712

[52] U.S. Cl.................... 260/465 E; 260/556 AR; 260/556 B; 260/465 D; 424/248; 424/267; 424/321; 260/247.1 R; 260/268 S; 424/324
[51] Int. Cl.².............. C07C 143/80; C07D 211/54; C07D 295/08
[58] Field of Search ..... 260/556 AR, 556 B, 465 D, 260/465 E; 71/103

[56] References Cited
UNITED STATES PATENTS

| | | | |
|---|---|---|---|
| 3,121,084 | 2/1964 | Winberg | 260/268 |
| 3,681,406 | 8/1972 | Beck | 71/103 X |
| 3,709,936 | 1/1973 | Fridinger et al. | 71/103 X |
| 3,772,277 | 11/1973 | Beck | 71/103 X |
| 3,821,276 | 6/1974 | Mrozik | 260/465 E |
| 3,824,233 | 7/1974 | Friedman | 260/465 E X |
| 3,828,079 | 8/1974 | Mrozik | 260/465 E X |
| 3,829,492 | 8/1974 | Miller et al. | 260/465 E X |
| 3,832,155 | 8/1974 | Beck | 71/103 |
| 3,880,644 | 4/1975 | Beck | 71/103 X |
| 3,888,897 | 6/1975 | Martin | 260/465 E |

FOREIGN PATENTS OR APPLICATIONS

| | | | |
|---|---|---|---|
| 900,111 | 7/1962 | United Kingdom | 260/556 AR |
| 1,251,147 | 10/1971 | United Kingdom | 260/556 AR |
| 45-15,254 | 2/1967 | Japan | 260/556 AR |

*Primary Examiner*—Allen B. Curtis
*Attorney, Agent, or Firm*—J. Jerome Behan; David L. Rose

[57] ABSTRACT

Novel substituted benzenesulfonamides are disclosed in which the sulfonamido nitrogen is substituted with various amino or alkoxy alkylene groups. The compounds are active anthelmintic agents and are particularly active against mature and immature fasciola. Processes for their preparation utilizing novel intermediates as well as compositions and methods for the treatment of helminthiasis are also disclosed.

21 Claims, No Drawings

ANTHELMINTIC SUBSTITUTED SULFONAMIDE DERIVATIVES

SUMMARY OF THE INVENTION

This invention relates to novel sulfonamides and to methods for their preparation. In particular this invention relates to novel 3,4,5-substituted benzenesulfonamides in which the sulfonamido nitrogen is doubly bonded to an amino alkylene or an alkoxy alkylene group which may also be variously substituted These novel compounds have antiparasitic and anthelmintic activity and are particularly active against liver fluke in sheep and cattle.

Thus, it is an object of this invention to provide for novel substituted benzenesulfonamides. It is a further object of this invention to provide for proesses for the preparation of such compounds. Another object is to provide for compositions and methods for the treatment of parasitic diseases using such compounds as the active ingredient. A still further object is to provide specifically for such compositions and methods which are useful against fasioliasis or liver fluke infection in sheep and cattle.

DESCRIPTION OF THE INVENTION

The novel compounds of this invention are represented by the following structural formula:

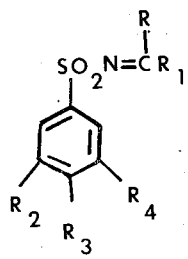

I wherein
R is hydrogen or loweralkyl;
$R_1$ is amino or mono or disubstituted amino wherein the substituents are independently selected from loweralkyl, carboxymethylene or phenyl; morpholino, N'-loweralkyl piperazinyl or loweralkoxy, provided that when one of the amino substituents is methyl the other substituent must be other than methyl.
$R_2$ is halo, nitro or perfluoroloweralkyl
$R_3$ is hydrogen or amino; and
$R_4$ is cyano or $R_2$ As employed in the instant description, the term "loweralkyl" is defined as including alkyl groups of from 1 to 6 carbon atoms such as methyl, ethyl, propyl, butyl, pentyl and hexyl as well as branched isomers thereof.

The term "loweralkoxy" is defined as including those alkoxy groups containing from 1 to 6 carbon atoms such as methoxy, ethoxy, propoxy, butoxy, pentoxy or hexoxy as well as branched isomers thereof.

The term "cycloalkoxy" is defined as the cyclic hydrocarbon rings containing from 5 to 8 carbon atoms such as cyclopentoxy, cyclohexoxy, cycloheptoxy, and cyclooctoxy.

The term "halo" or "halogen" is defined as including the halogen atoms fluorine, chlorine, bromine and iodine.

It is also intended that certain salts of the above compounds be included within the ambit of this invention. These salts are the acid addition salts formed from mineral acids, such as hydrochloric, sulfuric, phosphoric acids and the like, or organic acids such as acetic, propionic, citric acid and the like, when a suitable basic group, such as an amine function is present on the molecule. Also included are the salts formed from alkali metal and alkaline earth metal bases such as hydrides, hydroxides, carbonates, bicarbonates and the like, when there is a suitable acid function, such as carboxy, present on the molecule.

The novel compounds of this invention are useful as antiparasitic and anthelmintic agents. They are preferentially employed in the treatment of fascioliasis in sheep and cattle and when so employed are combined with non-toxic carriers for either oral or parenteral use. These compositions and their method of use in treating liver fluke infestations thus form other aspects of this invention.

PREFERRED EMBODIMENTS OF THE INVENTION

The preferred embodiments of this invention are realized in the following structural formula:

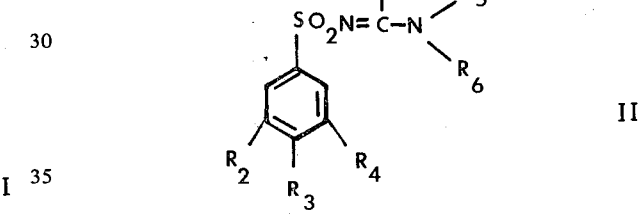

II wherein R $R_2$, $R_3$ and $R_4$ are as previously defined and $R_5$ and $R_6$ are hydrogen and loweralkyl such that only one of $R_5$ and $R_6$ is hydrogen in a given molecule providing that $R_5$ and $R_6$ are not both methyl in the same molecule. Further preferred embodiments are realized in the following structural formula:

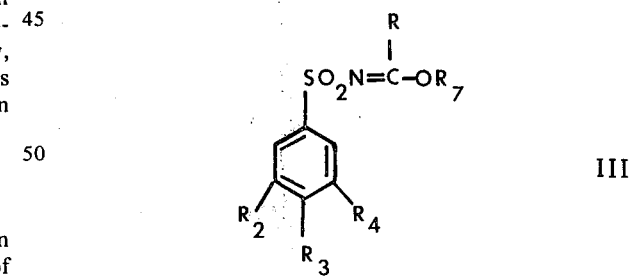

III wherein $R_2$, $R_3$ and $R_4$ are as previously defined and $R_7$ is loweralkyl.

Especially preferred compounds of this invention are realized when in the above preferred formulae R is chloro, bromo, iodo, trifluoromethyl or nitro; $R_3$ is hydrogen; and $R_4$ is chloro, bromo, iodo, trifluoromethyl, nitro or cyano.

The compounds of the present invention including the compounds of structure I wherein $R_1$ is dimethylamino have utility in the field of animal therapy. They are effective anthelmintics and are especially effective against both mature and immature liver fluke of the species *Fasciola gigantica* and *Fasciola hepatica*, the common liver fluke in sheep and cattle. The preferred dosage levels depend on the type of compound to be employed, the type of animal to be treated, the particular helminth to be combatted, and the severity of the helminthic infestation. In general, effective fluke eradication is achieved when the compounds are administered orally at dosage levels of from about 1 to 300 mg/kg of animal body weight and preferably from about 5 to 100 mg/kg of animal body weight. The compounds of the present invention may be administered in a variety of ways depending upon the particular animal employed, the type of anthelmintic treatment normally given to such animal, the materials employed and the particular helminths being combatted. It is preferred to administer them in anthelmintically effective amounts in a unit oral or parenteral, most preferably oral, dose at a time when fluke infection is apparent or suspected in the animal.

In addition to the inactive ingredients in the composition, said composition may contain one or more other active ingredients which may be selected from the compounds described by Formula I or from other known anthelmintic agents. Beneficial results are obtained when the compounds of Formula I are combined with an anthelmintic agent such as thiabendazole (2-(4-thiazolyl)benzimidazole), tetramisole (dl-2,3,5,6-tetrahydro-6-phenylimidazo-[2,1-b]thiazole), rafoxanide (3,5-diiodo-3'-chloro-4'-(p-chlorophenoxy)salicylanilide), fenbendazole (methyl-5-phenylthio-2-benzimidazole carbamate) and phenothiazine, known anthelmintic agents.

In general, compositions containing the active anthelmintic compound are employed. The amounts of the anthelmintic ingredient in the composition as well as the remaining constituents vary according to the type of treatment to be employed, the host animal and the particular helmintic infestation being treated. In general, however, compositions suitable for oral administration, containing a total weight percent of the active compound or compounds ranging from 0.01 to 95 percent will be suitable with the remainder of the compositions being any suitable carrier or vehicle. A number of modes of treatment may be employed and each to some extent determines the general nature of the composition. For example, the anthelmintic compounds may be administered to domesticated animals in a unit oral dosage form such as a tablet, bolus, capsule, or drench; a liquid oil base form suitable for parenteral administration or they may be compounded as a feed premix to be later admixed with the animals feedstuff. When the compositions are to be solid unit dosage forms as in tablets, capsules or boluses, the ingredients other than the active compounds may be any other non-toxic vehicle convenient in the preparation of such forms and preferably materials nutritionally suitable such as starch, lactose, talc, magnesium stearate, vegetable gums, and the like. Moreover, when capsules are employed, the active compound may be used in essentially undiluted form, the only extraneous material being that of the capsule casing itself which may be hard or soft gelatin or any other acceptable encapsulating material. When the dosage form is to be used for parenteral administration the active material is suitable admixed with an acceptable oil base vehicle preferably of the vegetable oil variety such as peanut oil, cotton seed oil and the like. In all such forms, that is, in tablets, boluses, capsules and oil base formulations, the active compound conveniently ranges from about 5 to 80 percent by weight of the total composition.

When the compounds are used in the form of a drench, the anthelmintic agents may be mixed with or adsorbed on agents which will aid in the subsequent suspending of the active compounds in water such as bentonite, clays, silica, water soluble starches, cellulose derivatives, gums, surface active agents and the like to form a dry pre-drench composition, and this pre-drench composition is added to water just before use. In the pre-drench formulation, in addition to the suspending agent, such ingredients as preservatives, antifoam compounds or other suitable diluents or solvents may be employed. Such a dry product may contain as much as 95 percent by weight of the active compound, the rest being excipient. Preferably, the solid composition contains from 30 to 95 percent by weight of the active compound. Enough water should be added to the solid product to provide the proper dosage level with a convenient amount of liquid for a single oral dose. The commonly used measure in the field is 1 fluid ounce of material and thus 1 fluid ounce of a drench should contain enough of the anthelmintic compound to provide an effective dosage level. Liquid drench formulations containing from 10 to 50 percent by weight of dry ingredients will in general be suitable with a preferred range being from 15 to 25 weight percent.

When the compositions are intended to be used in feeds, feed supplements or feed premixes, they will be mixed with suitable ingredients of the animals nutrient ration. Solid orally ingestible carriers normally used for such purposes such as distillers dried grains, corn meal, citrus meal, fermentation residues, ground oyster shells, attapulgus clay, wheat shorts, molasses solubles, corn cob meal, vegetable substances, toasted dehulled soya flour, soya bean meal feed, antibiotic mycellia, soya grits, crushed limestone and the like are all suitable. The active compounds are intimately dispersed or admixed throughout the active solid carrier by methods such as grinding, milling, or tumbling. By selecting a proper diluent and by altering the ratio of carrier to active ingredient, compositions of any desired concentration may be prepared. Feed supplement formulations containing from about 10 to 30 percent of active ingredient are particularly suitable for addition to feeds. The active compound is normally dispersed or mixed uniformly in the diluent but in some instances may be adsorbed on the carrier.

These supplements are added to the finished animal feed in an amount adequate to give the final concentration desired for controlling or treating the helminth infection by way of animal ration. Although the preferred level in feeds will depend on the particular compounds being employed, the active compounds of this invention are normally fed at levels of 0.01 to 3 percent by weight. As stated above, animals are preferably treated at a time when the infestation is apparent or suspected and the most preferred method of such treatment is with single oral doses. Thus, administration of medicated feed is not preferred but may be employed. Similarly, the amounts of drug present in the feed may be reduced to levels in the order of 0.01 to 0.5 percent by weight, based on the weight of the feed and the medicated feed administered over prolonged periods. This could be in the nature of a preventive or prophylactic measure. Another method of administering the compounds of this invention to animals whose feeds are conveniently pelleted such as sheep is to incorporate them directly into the pellets. FOr instance, the anthelmintic compounds are readily incorporated in the nutritionally adequate alfafa pellets at levels of 2 to 10 g. per pound for therapeutic use and lower levels for prophylactic use, and such pellets fed to the animals.

Examples of compositions suitable for administration to animals are:

A typical bolus composition is as follows: O-Ethyl-N-(3,5-dibromophenylsulfonyl)

| formimino ether | 1.0 g. |
|---|---|
| Dicalcium phosphate | 1.0 g. |
| Starch | 0.7 g. |
| Guar gum | 0.16 g. |
| Talc | 0.11 g. |
| Magnesium stearate | 0.028 g. |

A typical drench composition is as follows: O-Ethyl-N-(3-bromo-5-cyanophenylsulfonyl)

| formimino ether | 1.2 g. |
|---|---|
| Benzalkonium chloride | 0.6 g. |
| Antifoam emulsion | 0.06 g. |
| Hydroxyethyl cellulose | 0.3 g. |
| Sodium phosphate monobasic | 0.3 ml. |
| Water | q.s. 30 ml. |

Examples of typical feed premix supplements are as follows:

| A. N,N-dimethyl-N'-(3-iodo-5-trifluoromethyl-phenylsulfonyl) formamidine | 10 lbs. |
|---|---|
| Corn meal | 90 lbs. |
| B. N,N-dimethyl-N'-(3-Bromo-5-cyano-phenylsulfonyl) formamidines | 20 lbs. |
| Soybean mill feed | 80 lbs. |

The above feed premix supplements are combined with the animals regular feed, intimately mixing therewith such that the final concentration of the active ingredient is from 0.01 to 3 percent by weight.

The compounds of the instant invention are prepared by processes which are best visualized in the following reaction scheme.

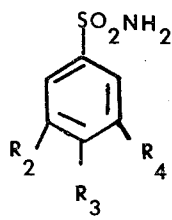

IV

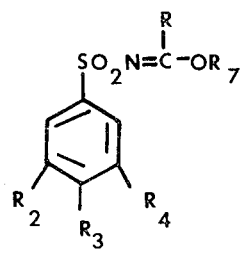

III

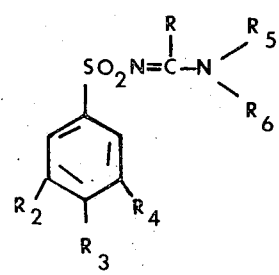

II wherein R, $R_2$, $R_3$, $R_4$ and $R_7$ are as previously defined; and $R_5$ and $R_6$ are each hydrogen, loweralkyl, carboxymethylene or phenyl; provided that $R_5$ and $R_6$ are not both methyl in the same molecule; $R_5$ and $R_6$ may also be combined to form in combination with the nitrogen atom to which they are attached, a morpholino or an N'-loweralkylpiperazinyl group.

In the first step of this reaction procedure, a 3,4,5-substituted benzenesulfonamide (IV) is reacted with an orthoester of the formula: $RC(OR_7)_3$ wherein R and $R_7$ are as previously defined in order to form the loweralkoxyalkylene derivative (III). Any loweralkylorthoester may be employed, the product being dependent upon the particular ester employed. The reaction is generally run in an aprotic solvent such as chloroform, benzene, toluene, acetone, tetrahydrofuran and the like. The use of a solvent is however optional and the product may be obtained in equally good yields without any solvent. The reaction is run at from room temperature to the reflux temperature of the reaction medium and is complete in from 15 minutes to 6 hours. There is generally employed an excess of the orthoester over the sulfonamide although exactly one molar equivalent may be employed if desired. The product is recovered by techniques known to those skilled in this art.

The formamidine compounds II are prepared from the loweralkoxymethylene compounds (III) by treating the latter compound with an amine having the formula:

wherein $R_5$ and $R_6$ are as above defined in an optional aprotic solvent at from room temperature to the reflux temperature of the reaction mixture when a solvent is employed, and to 150°C. when no solvent is employed. The reaction is complete in from ½ to 6 hours and the product is isolated by techniques known to those skilled in this art. One molar equivalent of the amine is required for the completion of this reaction, however, generally an excess of the amine, up to about 10 molar equivalents, is generally employed.

Where it is desired to prepare an acid-addition salt of those compounds which have a suitable basic function with which such an acid can be coupled, the compound is dissolved in any solvent and said solution is then treated with the mineral or organic acid desired. The solvent is preferably one in which the free base is soluble and the salt is insoluble facilitating the isolation of the salt. This is not necessary, however, and high conversion rates of pure salts are achieved with solvents not meeting this criteria.

Where it is desired to prepare an alkali metal or alkaline earth metal salt of a compound bearing an acid function, techniques similar to those employed for acid-addition salts are employed. The compound bearing the acid function is dissolved or suspended in a suitable solvent which must not react with the base aprotic solvents are preferred. The base is then added to the acidic compound and the salt isolated by techniques known to those skilled in this art.

When it is desired to prepare derivatives of the instant compounds wherein R is other than hydrogen a procedure starting with the N-unsubstituted benzenesulfonamide as outlined in the following reaction scheme is employed:

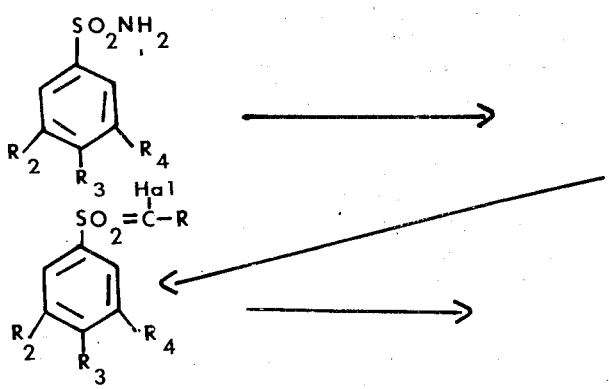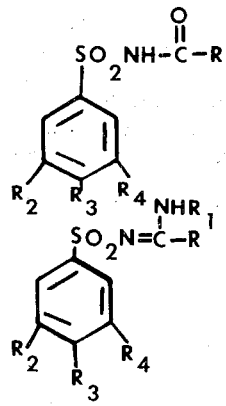

wherein R, $R_1$, $R_2$, $R_3$ and $R_4$ are as previously defined, and Hal is a halogen atom.

The benzenesulfonamide is first treated with a base such as an alkali metal or alkaline earth metal hydroxide, hydride, alkoxide and the like and the thus formed alkali metal or alkaline earth metal salt is treated with an acylating agent such as a loweralkyl carboxylic acid anhydride, acid chloride and the like. Other acylating agents known to those skilled in the art may also be employed. The reaction is run in an aprotic solvent such as benzene, toluene, dimethylformamide, tetrahydrofuran and the like. The product formed is the N-acyl benzene sulfonamide or sulfanilamide wherein the acyl group is substituted on the sulfonamide nitrogen. The salt formation reaction is run at from 0° to 75°C. for from 5 minutes to 3 hours. There is very often noticed an initial exothermic reaction which may require external cooling.

The alkali metal or alkaline earth metal salt is generally used in situ as it is formed.

The acylation reaction is run at from room temperature to the reflux temperature of the reaction mixture for from 30 minutes to 5 hours. The product is isolated by techniques known to those skilled in this art and is generally used without further purification in subsequent reactions.

The acyl compound is then treated with a halogenating agent such as phosphorous pentahalide, phosphorous oxyhalide, thionyl halide, phosgene and the like. The chlorinating agents are the preferred reagents exemplified by phosphorous pentachloride, phosphorous oxychloride, thionyl chloride, phosgene and the like. A combination of halogenating agents may also be employed where such a combination is beneficial for improved reactivity, stability or to insure the fluidity of the reaction medium. In addition, an optional solvent may be employed if such solvent will not interfere with the reaction. Aprotic solvents such as benzene, toluene, or other aromatic hydrocarbons, or other aprotic solvents as chlorobenzene, ethers and the like. The reaction is run at from 0°C. to the reflux temperature for from 5 minutes to 6 hours and the product is isolated by procedures known to those skilled in the art. The product formed is an imidoyl halide as shown in the above reaction scheme.

The thus formed imidoyl halide is then treated with ammonia or a primary or secondary amine to form the desired substituted amidine. The reaction is run with an excess of the ammonia or the amine to neutralize the hydrogen halide liberated during the course of the reaction. Optionally a non-reactive base such as a tertiary amine or an inorganic base may be employed in the reaction. The reaction is run at from room temperature to the reflux temperature of the reaction medium for from 5 minutes to 24 hours. The less basic amines such as the aromatic amines generally require longer heating times and higher temperatures than the more basic loweralkyl amines and ammonia. A solvent may be employed such as aliphatic and aromatic hydrocarbons, chlorinated aliphatic and aromatic hydrocarbons, ethers, tertiary amines and the like. In addition, the reacting amines may be used in such excess as to become a solvent for the reaction. The product is isolated from the reaction mixture and purified by techniques known to those skilled this art.

The following Examples are typical of the procedures employed to synthesize the compounds of this invention. The Examples are presented so that the invention might be more fully understood and should not be construed as being limitative of the invention.

EXAMPLE 1

O-Ethyl-N(3,5-dibromophenylsulfonyl) formimino ether

315 Mg. (1 mmole) of 3,5-dibromobenzenesulfonamide and 1.0 ml. of triethylorthoformate (3.75 mmoles) are combined and heated in an oil bath at 130°C. for 30 minutes. A clear solution is formed which stops bubbling after 20 minutes. The reaction mixture is cooled whereupon it solidifies completely. The solid material is washed with ethanol, centrifuged, washed again with ethanol and dried in vacuo at 50°C. recovering white crystals, melting point 137° to 139°C. 360 Mg. of O-ethyl-N(3,5-dibromophenylsulfonyl) formimino ether is recovered.

EXAMPLE 2

O-Ethyl-N(3-iodo-5-cyanophenylsulfonyl) formimino ether 3.08 G. (10 mmoles) of 3-iodo-5-cyanobenzenesulfonamide and 10 ml. of triethylorthoformate are combined and heated in an oil bath at 130°C. with stirring. After 15 minutes a clear solution is formed and the reaction mixture starts to bubble which continues for 30 minutes. The reaction mixture is cooled to room temperature and allowed to stand for 1 hour. The reaction mixture is washed with ethanol, filtered, and washed again with ethanol affording a solid material melting at 138° to 140°C. 3.45 G. of a beige solid is recovered.

EXAMPLE 3

O-Methyl-N(3,5-ditrifluoromethylphenylsulfonyl) formimino ether

293 Mg. (1 mmole) of 3,5-ditrifluoromethylbenzenesulfonamide and 1.0 ml. of trimethylorthoformate are combined and heated in an oil bath at 130°C. for 30 minutes. A clear solution is formed which bubbles for 20 minutes after reaching the reaction temperature. The reaction mixture is cooled whereupon it solidifies completely. The solid material is washed with methanol, centrifuged, washed again with methanol and dried in vacuo at 50°C. recovering white crystals of O-methyl-N(3,5-ditrifluoromethylphenylsulfonyl) formimino ether.

EXAMPLE 4

O-Butyl-N(3-bromo-5-cyanophenylsulfonyl) formimino ether 2.61 G. (10 mmoles) of 3-bromo-5-cyanobenzenesulfonamide and 10 ml. of tributylorthoformate are combined and heated in an oil bath at 130°C. with stirring. After 15 minutes a clear solution is formed and the reaction mixture starts to bubble which continues for 30 minutes. The reaction mixture is cooled to room temperature and allowed to stand for 1 hour. The reaction mixture is filtered, and washed with butanol affording crystalline O-butyl-N-(3-bromo-5-cyanophenylsulfonyl) formimimino ether.

EXAMPLE 5

O-Ethyl-N-(3-bromo-5-nitrophenylsulfonyl) formimino ether 2.81 G. (10 mmoles) of 3-bromo-5-nitrobenzenesulfonamide and 10 ml. of triethylorthoformate are combined and heated in an oil bath at 130°C. with stirring. After 15 minutes a clear solution is formed and the reaction mixture starts to bubble which continues for 30 minutes. The reaction mixture is cooled to room temperature and allowed to stand for 1 hour. It is filtered, and washed with ethanol affording crystalline O-ethyl-N-(3-bromo-5-nitrophenylsulfonyl) formimino ether.

EXAMPLE 6

N-Morpholinomethylene-3,5-dibromobenzenesulfonamide

371 Mg. (1 mmole) of O-ethyl-3,5-dibromophenylsulfonyl formimino ether and 870 mg. of morpholine are combined in 10 ml. of toluene and refluxed for 1 hour. The reaction mixture is concentrated to 2 ml. and allowed to crystallize. The solid material is collected by centrifugation and dried in vacuo at 50°C. affording crystalline material with a melting point of 189° to 191°C. 300 Mg. of N-morpholinomethylene 3,5-dibromobenzenesulfonamide is recovered. Recrystallization from dimethylsulfoxide/water affords a pure sample with a melting point of 195° to 197°C.

EXAMPLE 7

N,N-Dimethyl-N'-(3,5-dibromophenylsulfonyl) formamidine

371 Mg. (1 mmole) of O-ethyl-N-(3,5-dibromophenylsulfonyl) formimino ether is dissolved in 10 ml. of toluene at 35°C. Gaseous dimethylamine is bubbled through the solution for 5 minutes maintaining the temperature at 35°C. The reaction mixture is stirred overnight at room temperature whereupon some crystallization is observed. The reaction mixture is concentrated by heating in an oil bath at 170°C. Upon cooling to room temperature, the reaction mixture solidifies and is treated with ethyl acetate and filtered. The solid material is dried in vacuo at 50°C. affording 250 mg. of N,N-dimethyl-N'-(3,5-dibromophenylsulfonyl) formamidine, melting point 157° to 158°C. Recrystallization from dimethylsulfoxide/water gives pure N,N-dimethyl-N'-(3,5-dibromophenylsulfonyl) formamidine, melting point 160° to 162°C.

EXAMPLE 8

N,N-Di(2-hydroxyethyl)-N'-(3,5-dibromophenylsulfonyl) formamidine

371 Mg. (1 mmole) of O-ethyl-N-(3,5-dibromophenylsulfonyl) formimino ether is dissolved in 10 ml. of toluene at 35°C. 1.05 G. of diethanolamine is added and the reaction mixture is refluxed for several hours. Then chloroform is added and the organic solution washed with water, dried over magnesium sulfate and concentrated in vacuo to a colorless oil which solidifies. It is recrystallized from an acetone-ether mixture, giving N,N-di(2-hydroxyethyl)-N'-(3,5-dibromophenylsulfonyl) formamidine with a melting point of 118°C.

EXAMPLE 9

N,N-Dimethyl-N'-(3-cyano-5-iodophenylsulfonyl) formamidine

A solution of 364 mg. (1 mmole) of O-ethyl-N-(3-iodo-5-cyanophenylsulfonyl) formimino ether in 10 ml. of toluene at 35°C. is treated with dimethylamine gas until the solution is saturated. A precipitate forms and the mixture is stirred for one half hour at 35°C. and filtered. The solid material is washed with toluene and ether and dried affording 281 mg. (77%) of N,N-dimethyl-N'-(3-cyano-5-iodophenylsulfonyl) formamidine, melting point to 186° to 187°C.

EXAMPLE 10

N-Methyl-N-carboxymethylene-N'-(3,5-ditrifluoromethylphenylsulfonyl) formamidine 670 Mg. (2 mmoles) of O-methyl-N-(3,5-ditrifluoromethylphenylsulfonyl) formino ether is dissolved in 20 ml. of toluene at 35°C. 196 Mg. of N-methylglycine is added and the reaction mixture is refluxed for several hours. Chloroform is added and the organic solution washed with water, dried over magnesium sulfate, and concentrated in vacuo affording N-methyl-N-carboxymethylene-N'-(3,5-ditrifluoromethylphenylsulfonyl) formamidine.

EXAMPLE 11

N-(4-Methylpiperazinylmethylene)-3-cyano-5-iodobenzenesulfonamide

A solution of 728 mg. (2 mmoles) of ethyl-N-(3-cyano-5-iodobenzenesulfonyl) formamidate in 25 ml. of toluene at 35°C. is treated with 0.50 ml. (452 mg., 4.5 mmoles) of 1-methylpiperazine. The reaction mixture is stirred at 35°C. for one hour and evaporated to dryness in vacuo. The solid residue is triturated with ether and the product taken up in methylene chloride, treated with charcoal, filtered, diluted with hexane and evaporated to dryness in vacuo affording a solid residue. The solid residue is dissolved in a minimum amount of methylene chloride and placed on a column of 20 g. of silica gel. The column is eluted with 5% methanol in methylene chloride and the product collected in 10 fractions that are combined, diluted with hexane and crystallized affording N-(4-methylpiperazinylmethylene)-3-cyano-5-iodo-benzenesulfonamide.

EXAMPLE 12

1,4-Bis-(3-cyano-5-iodophenylsulfonyl-aminomethylene) piperazine

A solution of 728 mg. (2 mmoles) of ethyl-N-(3-cyano-5-iodo-benzenesulfonyl) formimidate in 25 ml. of toluene at 35°C. is treated with a solution of 86 mg. (1 mmole) of piperazine in 10 ml. toluene. The reaction mixture becomes cloudy and a precipitate forms. The mixture is stirred for one and a half hours at room temperature and filtered. The product is washed with toluene and ether and dried affording 645 mg. of a solid material which is dissolved in hot dimethylformamide and diluted with water. The precipitate is filtered and washed with water, methanol and ether affording 454 mg. (63%) of 1,4-bis-(3-cyano-5-iodophenylsulfonylaminomethylene) piperazine.

EXAMPLE 13A

N-Acetyl-3-cyano-5-iodobenzenesulfonamide

A solution of 3.08 g. (10 mmoles) of 3-cyano-5-iodobenzenesulfonamide in 30 ml. of dimethylformamide is treated with 420 mg. (10 mmoles) of 57% sodium hydride emulsion. When the initial reaction subsides, the mixture is heated in a warm water bath for one hour. 2.8 Ml. (30 mmoles) of acetic anhydride is added and the solution becomes cloudy. The mixture is stirred for one hour and poured into an ice water mixture. After 30 minutes of stirring, the precipitate is filtered, washed with water, methanol and ether affording 2.97 g. (85%) of N-acetyl-3-cyano-5-iodobenzenesulfonamide melting point 249° to 251°C.

EXAMPLE 13B

N-(3-Cyano-5-iodophenylsulfonyl) acetimidoyl chloride

A suspension of 308 mg. (1 mmole) of the acetylsulfonamide of Example 13A in 6 ml. of benzene is treated with 228 mg. (1.1 mmoles) phosphorous-pentachloride and heated to reflux for one half hour 2 Ml. of phosphorous oxychloride is then added and the heating continued for another half hour whereupon an additional 2 ml. of phosphorous oxychloride is added. The mixture is refluxed for an additional hour and concentrated in vacuo. The residue on treatment with hexane crystallizes and the solid material is filtered and washed with hexane affording 275 mg. of a solid material which is washed with methylene chloride and filtered. The filtrate is diluted with hexane whereupon an oil separates. The solution is decanted, diluted with more hexane and evaporated down to a small volume. On scratching the product crystallizes affording 110 mg. of N-(3-cyano-5-iodophenylsulfonyl) acetimidoyl chloride melting point 101° to 104°C.

EXAMPLE 14

N-(3-Cyano-5-iodophenylsulfonyl) acetamidine

Ammonia gas is bubbled into a solution of 1.106 g. (3 mmoles) of crude N-(3-cyano-5-iodophenylsulfonyl) acetimidoyl chloride in methylene chloride affording a precipitate. The reaction mixture is filtered and the solution is boiled to a small volume. Upon the careful addition of hexane, 560 mg. of N-(3-cyano-5-iodophenylsulfonyl) acetamidine is precipitated with a melting point of 173° to 177°C. Repeated recrystallizations from methylene chloride hexane afford a product with a melting point of 177° to 178°C.

EXAMPLE 15

N-(3-Cyano-5-iodophenylsulfonyl)-N'-phenylacetamidine

A solution of 367 mg. (1 mmole) of N-(3-cyano-5-iodophenylsulfonyl) acetamidine in 10 ml. of chlorobenzene is heated with 205 mg. (2.2 mmoles) of aniline and the reaction mixture heated to reflux for 3 hours. The reaction mixture is cooled in an ice bath and filtered to remove the precipitate of aniline hydrochloride. The filtrate is treated with hexane affording crystalline N-(3-cyano-5-iodophenylsulfonyl)-N'-phenyl acetamidine.

EXAMPLE 16

N-(4-Amino-3,5-dibromophenylsulfonyl) acetimidoyl chloride

A mixture of 372 mg. of $N^1$-acetyl-3,5 dibromo sulfanilamide, 7.5 ml. of benzene, 5 ml. of phosphorous oxychloride and 230 mg. of phosphorous pentachloride is refluxed for 2 hours. The reaction mixture is cooled and concentrated in vacuo to an oil which solidified upon trituration with hexane. The solid material is filtered and washed with hexane affording N-(4-amino-3,5-dibromophenylsulfonyl) acetimidoyl chloride, which is used without further purification in the next step.

EXAMPLE 17

N,N-Diethyl-N'-(4-amino-3,5-dibromophenylsulfonyl) acetamidine

100 Mg. of crude N-(4-amino-3,5-dibromophenylsulfonyl) acetimidoyl chloride is stirred in 10 ml. of methylene chloride with 1 ml. of diethylamine at room temperature overnight. Volumes of water and methylene chloride equal to the volume of the reaction mixture are added, agitated and the layers separated. The organic layer is dried over magnesium sulfate and evaporated to dryness, in vacuo. The residue is taken up in 1 ml. of ethyl acetate and the dropwise addition of petroleum ether affords N,N-diethyl-N'-(4-amino-3,5-dibromophenylsulfonyl) acetamidine.

It will be appreciated that the instant specification and examples are set forth by way of illustration and not limitation, and that various modifications and changes may be made without departing from the spirit and scope of the present invention.

What is claimed is:
1. A compound having the formula:

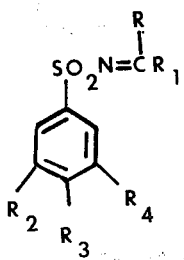

wherein R is hydrogen or loweralkyl; $R_1$ is amino or mono or disubstituted amino wherein the substituents are independently selected from loweralkyl, carboxymethylene and phenyl; or loweralkoxy provided that when one of the amino substituents is methyl the other substituent must be other than methyl; $R_2$ is halo, nitro or perfluoroloweralkyl; $R_3$ is hydrogen or amino; and $R_4$ is $R_2$ or cyano.

2. A compound having the formula:

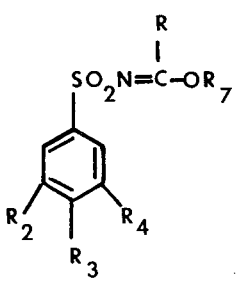

wherein R is hydrogen or loweralkyl; $R_2$ is halo, nitro or perfluoroloweralkyl; $R_3$ is hydrogen or amino; $R_4$ is $R_2$ or cyano; and $R_7$ is loweralkyl.

3. A compound having the formula:

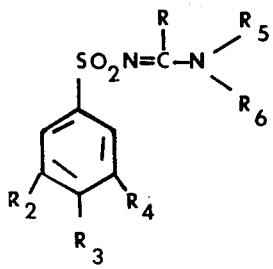

wherein R is hydrogen or loweralkyl; $R_2$ is halo, nitro or perfluoroloweralkyl; $R_3$ is hydrogen or amino; $R_4$ is $R_2$ or cyano; and $R_5$ and $R_6$ are each hydrogen, loweralkyl; carboxymethylene or phenyl, provided that when one of $R_5$ and $R_6$ is methyl the other is other than methyl.

4. A compound of claim 2 wherein $R_7$ is loweralkyl.
5. A compound of claim 4 wherein $R_7$ is ethyl.
6. A compound of claim 2 wherein $R_2$ is chloro, bromo, iodo, trifluoromethyl or nitro; $R_3$ is hydrogen and $R_4$ is chloro, bromo, iodo, trifluoromethyl, nitro or cyano.
7. A compound of claim 6 wherein $R_7$ is methyl or ethyl.
8. A compound of claim 7 which is O-ethyl N-(3,5-dibromophenylsulfonyl) formimino ether.
9. A compound of claim 7 which is O-ethyl N-(3-bromo-5-cyanophenylsulfonyl formimino ether.
10. A compound of claim 7 which is O-ethyl N-(3-iodo-5-trifluoromethyl phenylsulfonyl) formimino ether.
11. A compound of claim 7 which is O-ethyl N-(3-iodo-5-cyanophenylsulfonyl) formimino ether.

12. A compound of claim 3 wherein $R_5$ and $R_6$ are hydrogen or loweralkyl provided that when one of $R_5$ and $R_6$ is methyl the other is other than methyl.
13. A compound of claim 12 wherein $R_5$ is hydrogen and $R_6$ is methyl.
14. A compound of claim 3 wherein $R_2$ is chloro, bromo, iodo, trifluoromethyl or nitro; $R_3$ is hydrogen and $R_4$ is chloro, bromo, iodo, trifuoromethyl, nitro, or cyano.
15. A compound of claim 14 wherein $R_5$ and $R_6$ are hydrogen or loweralkyl provided that when one of $R_5$ and $R_6$ is methyl the other is other than methyl.
16. A compound of claim 15 which is N,N-diethyl-N'-(3,5-dibromophenylsulfonyl) formamidine.
17. A compound of claim 15 which is N,N-diethyl-N'-(3-bromo-5-cyanophenylsulfonyl) formamidine.
18. A compound of claim 15 which is N,N-diethyl-N'-(3-iodo-5-trifluoromethylphenylsulfonyl) formamidine.
19. A compound of claim 15 which is N,N-diethyl-N'-(3-iodo-5-cyanophenylsulfonyl) formamidine.
20. A process for the preparation of a compound having the formula:

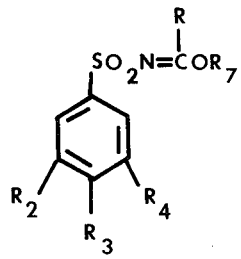

wherein R is hydrogen or loweralkyl; $R_2$ is halo, nitro, or perfluoroloweralkyl; $R_3$ is hydrogen or amino; $R_4$ is $R_2$ or cyano; and $R_7$ is loweralkyl which comprises treating a benzenesulfonamide having the formula:

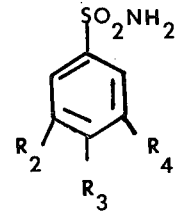

wherein $R_2$, $R_3$ and $R_4$ are as previously defined, with an orthoester having the formula: $RC(OR_7)_3$ wherein R and $R_7$ are as previously defined.

21. A process for the preparation of a compound having the formula:

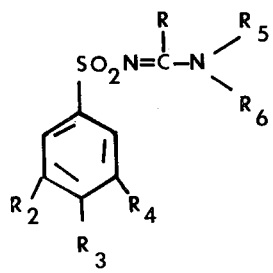

wherein R is hydrogen or loweralkyl; $R_2$ is halo, nitro or perfluoroloweralkyl; $R_3$ is hydrogen or amino; $R_4$ is $R_2$ or cyano; and $R_5$ and $R_6$ are each hydrogen, loweralkyl, carboxymethylene or phenyl, provided that when one of $R_5$ and $R_6$ is methyl, the other is other than methyl, which comprises treating a compound having the formula:

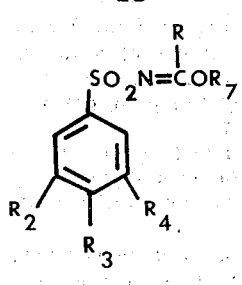
wherein R, $R_2$, $R_3$ and $R_4$ are as previously defined and $R_7$ is loweralkyl, with a compound having the formula:
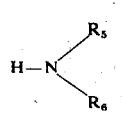
wherein $R_5$ and $R_6$ are as previously defined.
* * * * *